United States Patent
Matsumoto et al.

(10) Patent No.: US 9,005,638 B2
(45) Date of Patent: Apr. 14, 2015

(54) COSMETICS CONTAINING A MULTI-FUNCTIONAL COMPOSITE POWDER

(75) Inventors: Shuji Matsumoto, Kitakyushu (JP);
Naoyuki Enomoto, Kitakyushu (JP);
Yasutaka Miyoshi, Kawasaki (JP);
Takumi Miyazaki, Kitakyushu (JP)

(73) Assignee: JGC Catalysts and Chemicals Ltd., Kawasaki-Ku, Kanagawa (JP)

( * ) Notice: Subject to any disclaimer, the term of this patent is extended or adjusted under 35 U.S.C. 154(b) by 452 days.

(21) Appl. No.: 12/311,697

(22) PCT Filed: Jul. 31, 2007

(86) PCT No.: PCT/JP2007/064997
§ 371 (c)(1),
(2), (4) Date: Apr. 9, 2009

(87) PCT Pub. No.: WO2008/044385
PCT Pub. Date: Apr. 17, 2008

(65) Prior Publication Data
US 2010/0021509 A1    Jan. 28, 2010

(30) Foreign Application Priority Data
Oct. 12, 2006   (JP) .................. 2006-278191

(51) Int. Cl.
| A61K 8/02 | (2006.01) |
| A61K 8/29 | (2006.01) |
| A61K 8/19 | (2006.01) |
| A61Q 90/00 | (2009.01) |
| A61K 8/26 | (2006.01) |
| A61Q 1/12 | (2006.01) |
| C09C 1/00 | (2006.01) |

(52) U.S. Cl.
CPC .............. *A61K 8/19* (2013.01); *A61K 8/0258* (2013.01); *A61K 8/26* (2013.01); *A61K 8/29* (2013.01); *A61K 2800/412* (2013.01); *A61K 2800/621* (2013.01); *A61Q 1/12* (2013.01); *C01P 2004/61* (2013.01); *C09C 1/0015* (2013.01); *C09C 1/0081* (2013.01); *C09C 2200/102* (2013.01); *C09C 2200/505* (2013.01)

(58) Field of Classification Search
CPC ............. A61K 2800/412; A61K 2800/621; A61K 8/0258; A61K 8/19; A61K 8/26; A61K 8/29; A61Q 1/12; C01P 2004/61; C09C 1/0015; C09C 1/0081; C09C 2200/102; C09C 2200/505
USPC .......................... 424/401, 647, 617
See application file for complete search history.

(56) References Cited

U.S. PATENT DOCUMENTS

| 3,711,308 | A | * | 1/1973 | Brand et al. .................. 106/417 |
| 5,188,831 | A | | 2/1993 | Nicoll et al. |
| 5,626,661 | A | * | 5/1997 | Schmid et al. ................ 106/415 |
| 6,562,323 | B1 | | 5/2003 | Miyazaki et al. |
| 6,743,285 | B1 | | 6/2004 | Anselmann et al. |
| 7,485,183 | B2 | | 2/2009 | Hochstein et al. |
| 2003/0147819 | A1 | * | 8/2003 | Watanabe ...................... 424/63 |
| 2004/0191198 | A1 | | 9/2004 | Hochstein et al. |
| 2006/0034879 | A1 | | 2/2006 | Miyazaki et al. |

FOREIGN PATENT DOCUMENTS

| DE | 199 41 607 A1 | 3/2001 |
| DE | 103 29 780 A1 | 10/2004 |
| EP | 1 672 036 A1 | 6/2006 |
| JP | 48-72341 | 9/1973 |
| JP | 6-16527 A | 1/1994 |
| JP | H07-330542 | 12/1995 |
| JP | 11-43626 A | 2/1999 |
| JP | 11-189513 A | 7/1999 |
| JP | H11-343222 | 12/1999 |
| JP | 2000-273352 A | 10/2000 |
| JP | 2002-3744 A | 1/2002 |
| JP | 2002-68930 A | 3/2002 |

OTHER PUBLICATIONS

European Patent Office, Extended Search Report in European Patent Application No. 07 09 1681, (Aug. 24, 2012).
"Saishin Keshohin Kagaku", *Society of Cosmetic Chemists of Japan*, pp. 367-369, (1992).
Tamio Noguchi; *Fragrance Journal*, vol. 28, No. 5, pp. 58-64 (2000).
Masae Iida; *Fragrance Journal*, vol. 30, No. 7, pp. 23-27 (2002).
Akihito Sakai; *Fragrance Journal*, vol. 31, No. 4, pp. 81-91, (2003).
Takahashi et al.; *Fragrance Journal*, vol. 34, No. 2, pp. 67-73 (2006).
Takanori Igarashi; *Fragrance Journal*, vol. 34, No. 6, pp. 17-28, (2006).

\* cited by examiner

*Primary Examiner* — Janet Epps-Smith
*Assistant Examiner* — Courtney Brown
(74) *Attorney, Agent, or Firm* — Leydig, Voit & Mayer, Ltd.

(57) ABSTRACT

This invention provides cosmetics containing a multi-functional composite powder having the properties of (a) an excellent adhesiveness, (b) an excellent extendability, (c) an appropriate glossy effect, (d) a homogeneous cosmetic film, (e) an appropriate covering capability, (f) a cosmetic film not causing a white masking, (g) a high compatibility between a color appearance of cosmetics and a color tone of the cosmetic film, (h) an excellent soft-focusing capability, (i) an excellent ultraviolet protective effect, and the like. The multi-functional composite powder is constituted by a scale-like base material, a group of particles comprising at least fine particles of titanium dioxide deposited on a surface of the scale-like base material, and a thin film of a composite oxide containing titanium and iron coated thereon.

13 Claims, 1 Drawing Sheet

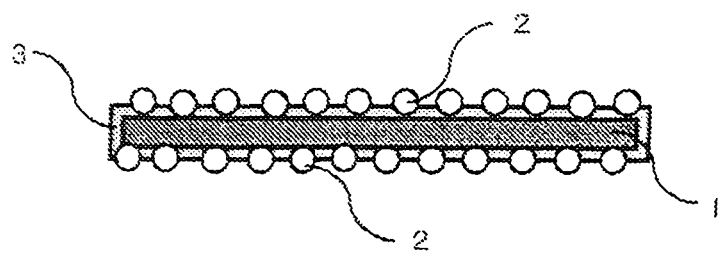

COSMETICS CONTAINING A MULTI-FUNCTIONAL COMPOSITE POWDER

BACKGROUND OF THE INVENTION

1. Technical Field

The present invention relates to cosmetics containing a composite powder obtained by depositing fine particles of titanium dioxide or the like on a surface of a scale-like base material, and more specifically relates to make-up cosmetics containing such a composite powder.

2. Background Technology

Generally, a scale-like powder made from mica, talc, sericite and the like is blended in make-up cosmetics such as powder foundations. When the scale-like powder is blended in the cosmetics, adhesiveness to and extendability of the cosmetics on a human skin are improved, and an appropriate glossy effect is given to a cosmetic film applied on the human skin. Therefore, the scale-like powder is indispensable for the make-up cosmetics.

Furthermore, in addition to the adhesiveness, extendability, and glossy effect as described above, it is required for the make-up cosmetics that;
(1) a homogeneous cosmetic film is formed on a human skin;
(2) an appropriate covering capability is provided; and
(3) a white masking is not appeared, even when a cosmetic film applied on a facial skin is looked from a specific angle.
Moreover, a soft-focusing capability and an ultraviolet protective capability are often required for the cosmetics.

The scale-like powder itself does not have a high covering capability, and therefore generally fine particles of titanium dioxide (as a white pigment) are blended in the cosmetics.

However, it is known that because the fine particles of titanium dioxide have a high covering capability, sometimes the cosmetics film formed on a human skin, in particular a facial skin, causes a white masking when it is looked from a specific angle, even when a foundation with a color adjusted to a color of the human skin is used. In addition, because the fine particles of titanium dioxide is relatively small, for instance with an average particle diameter of around 0.3 µm, it is difficult to prepare powdery cosmetics containing the fine particles homogeneously dispersed therein. Furthermore, sometimes the fine particles of titanium dioxide are present in the cosmetics in the state of those partially aggregated. For this reason, when the cosmetics are applied on a human skin, a remarkable whiteness may occur on the human skin at the places where the aggregated particles are collapsed when rubbed by hand or in areas around such places, although the whiteness is not so remarkable in the appearance of the cosmetics. Namely, sometimes the color appearance of the cosmetics is largely different from a color tone of the cosmetic film when the cosmetics are applied on the human skin. Furthermore, when the cosmetics are applied on a human skin, some persons may feel unsmoothness or squeakiness due to the fine particles of titanium dioxide, which may spoils the skin feelings in use of the cosmetics, for instance in the extendability or adhesiveness as described above.

To overcome the problems as described above, there has been proposed an extender pigment for cosmetics, which is prepared by depositing fine particles of titanium dioxide (as a white pigment) on a surface of a scale-like base material, to give a comfortable feeling to the human skin and also an excellent covering capability to the cosmetic film (Reference is made to Patent document 1). However, the extender pigment itself has not the ultraviolet protective capability and as the color is white, sometimes the cosmetics film formed on a human skin, in particular a facial skin, causes a white masking as described above. Therefore, all of the basic properties required for the make-up cosmetics are not obtained by using such an extender pigment.

The scale-like powder does not protect the human skin against ultraviolet rays, and therefore, to give the ultraviolet protective effect to cosmetics, an organic ultraviolet absorber or fine particles of titanium dioxide having a particle diameter of several tens nanometer as the primary particle size (hereinafter referred to as "nanoparticles of titanium dioxide") with an ultraviolet protective capability are often blended in the cosmetics. However, as the organic ultraviolet absorber causes a skin irritation, there is an upper limit to the amount of such ultraviolet absorber in practical use. Also, the average particle diameter of the nanoparticles of titanium dioxide is smaller than the fine particles of titanium dioxide as described above (namely, the average particle diameter of the nanoparticles of titanium dioxide is about several tens nanometer, while that of the fine particles of titanium dioxide is around 0.3 µm), and therefore it is extremely difficult to homogeneously disperse the nanoparticles of titanium dioxide in cosmetics such as powdery foundations. Furthermore, as the nanoparticles of titanium dioxide are often present in the aggregated state in several portions of the cosmetics, sometimes a color appearance of the cosmetics is substantially different from a color tone of the cosmetic film, like in the case of the fine particles of titanium dioxide as described above. Moreover, when the cosmetics are applied onto a human skin, many persons may feel unsmoothness or squeakiness strongly due to the nanoparticles of titanium dioxide, which may substantially spoils the skin feelings in use of the cosmetics, for instance in the extendability or adhesiveness as described above.

As described above, it is known that although various types of raw materials (such as extender pigments or color pigments) to be used in make-up cosmetics or the like show certain effects with the roles of the raw materials, such materials have various defects as described above. To overcome the problems, recent cosmetic manufacturers tend to prepare, by making the blending ratios of various raw materials in a balanced level, the cosmetics having the basic properties as described above, namely (a) an excellent adhesiveness, (b) an excellent extendability, (c) an appropriate glossy effect, (d) a homogeneous cosmetic film, (e) an appropriate covering capability, (f) a cosmetic film not causing a white masking, (g) a high compatibility between a color appearance of cosmetics and a color tone of the cosmetic film, (h) an excellent soft-focusing capability, (i) an excellent ultraviolet protective effect and the like. However, a sophisticated blending technique to obtain such basic properties as described above is required for preparation of the cosmetics. Even when the sophisticated blending technique is employed, it is not always possible to satisfy all of the above basic properties required for the cosmetics.

Patent document 1: Japanese Patent No. 3745688

DISCLOSURE OF THE INVENTION

Problems to be Solved by the Invention

The present inventors made serious efforts for developing cosmetics capable of satisfying the basic properties required for the make-up cosmetics or the like by blending only one type of a composite powder without using the sophisticated blending technique as described above. As a result, they found that such cosmetics can be obtained with use of a multi-functional composite powder prepared by depositing a group of particles comprising at least fine particles of titanium dioxide on a surface of a scale-like base material, and then coating a composite oxide containing titanium and iron thereon, and then completed the present invention.

That is, an objective of the present invention is to provide cosmetics, especially make-up cosmetics containing therein a multi-functional composite powder having the basic properties of (a) an excellent adhesiveness, (b) an excellent extendability, (c) an appropriate glossy effect, (d) a homogeneous cosmetic film, (e) an appropriate covering capability, (f) a cosmetic film not causing a white masking, (g) a high compatibility between a color appearance of cosmetics and a color tone of the cosmetic film, (h) an excellent soft-focusing capability, (i) an excellent ultraviolet protective effect, and the like.

Means for Solving the Problems

The cosmetics according to the present invention contain a multi-functional composite powder constituted by a scale-like base material, a group of particles comprising at least fine particles of titanium dioxide deposited on a surface of the scale-like base material, and a thin film of a composite oxide containing titanium and iron coated thereon.

Furthermore, it is preferable that the group of particles as described above further contains fine particles of ferric oxide in the range from 0.01 to 10.0% by weight.

The fine particles of titanium dioxide are preferably those having a white color, which are used as a color pigment.

The fine particles of ferric oxide are preferably those having a red-brown color, which are used as a color pigment.

Furthermore, the fine particles of titanium dioxide and the fine particles of ferric oxide are preferably those having been subjected to a surface treatment with oxides, hydroxides, and/or hydrous oxides of one or more metal elements selected from the group consisting of silicon, aluminum, zinc, and iron.

The multi-functional composite powder contains the fine particles of titanium dioxide deposited on a surface of the scale-like base material, preferably in the range from 5 to 30% by weight.

Furthermore, the multi-functional composite powder contains the thin film of the composite oxide coated thereon, preferably in the range from 10 to 30% by weight.

The composite oxide contains titanium and iron at a weight ratio ($Fe_2O_3/TiO_2$) being preferably in the range from 0.01 to 0.3, when the titanium is represented as $TiO_2$ and the iron is represented as $Fe_2O_3$.

The cosmetics contain the multi-functional composite powder preferably in the range from 5 to 60% by weight.

Furthermore, it is preferable that the cosmetics do not contain fine particles of titanium dioxide as a color pigment other than the multi-functional composite powder.

The cosmetics according to the present invention are preferable to be make-up cosmetics.

Effects of the Invention

According to the present invention with use of the multi-functional composite powder as described above, it is possible to easily obtain, without using other composite powders or color pigments, cosmetics having the properties of (a) an excellent adhesiveness, (b) an excellent extendability, (c) an appropriate glossy effect, (d) a homogeneous cosmetic film, (e) an appropriate covering capability, (f) a cosmetic film not causing a white masking, (g) a high compatibility between a color appearance of cosmetics and a color tone of the cosmetic film, (h) an excellent soft-focusing capability, (i) an excellent ultraviolet protective effect and the like.

When the cosmetics containing a multi-functional composite powder prepared with use of the fine particles of titanium dioxide and the fine particles of ferric oxide as the group of the particles to be deposited on a scale-like base material are applied onto a human skin, a cosmetic film with a reddish flesh color can be formed onto the human skin.

As described above, because the composite powder to be used in the present invention has a multi-functional effect, the cosmetics, in particular make-up cosmetics, which are recently desired from the cosmetics industry, can easily be obtained without employing the sophisticated blending technique for preparation of the cosmetics.

BEST MODE FOR CARRYING OUT THE INVENTION

Cosmetics containing a multi-functional composite powder according to the present invention (sometimes hereinafter referred to as "composite power" simply) are described below in detail.

[Composite Powder 1]

The first multi-functional composite powder to be used in the present invention is constituted by a scale-like base material, a group of particles comprising at least fine particles of titanium dioxide deposited on a surface of the scale-like base material, and a thin film of a composite oxide containing titanium and iron coated thereon.

As for the above scale-like base material, any material generally used as an extender pigment for cosmetics may be used without any restriction, and the materials available for this purpose include, but not limited to, talc, mica, sericite, synthetic mica, plate-like silica, plate-like aluminum oxide, flaky glass powder, and aluminum-deposited film. Of these materials, mica is preferable, because mica is especially excellent in giving the adhesiveness, extendability and glossy effect onto a cosmetic film, and therefore it is preferable to use mica as the scale-like base material.

An average diameter of the scale-like base material is preferably in the range from 1 to 40 µm, and more preferably in the range from 5 to 30 µm, which is measured with use of a particle size measuring device as described below. When the average particle diameter is not more than 1 µm, the diameter of the obtained composite powder is too small, which makes it impossible to obtain the desired effects. When the average particle diameter is not less than 40 µm, sometimes a glossy effect by the obtained composite powder is too strong, which disadvantageously gives unpleasant appearance to a cosmetic film.

Furthermore, an average thickness of the scale-like base material is preferably in the range from 0.005 to 1 µm, and more preferably in the range from 0.01 to 0.5 µm. When the average thickness is not more than 0.005 µm, the obtained composite powder is too bulky, which disadvantageously causes increasing of an oil absorption into the composite powder, and therefore a sophisticated blending technique is required when the composite powder is blended in cosmetics. When the average thickness is not less than 1 µm, the extendability of a cosmetic film onto a human skin disadvantageously becomes lower.

As for the fine particles of titanium dioxide to be deposited on the scale-like base material, any material may be used without any specific restriction, on the condition that the material is expressed by the chemical formula of $TiO_2$ and has a white color.

However, an average particle diameter of the fine particles of titanium dioxide is preferably in the range from 0.1 to 0.4 μm, and more preferably in the range from 0.2 to 0.3 μm. When the average particle diameter is not more than 0.1 μm, the effect of scattering visible light is too low, which gives a low soft focusing effect to a cosmetic film. In addition, some person will feel unsmoothness or squeakiness in use of the cosmetics containing such a composite powder, and the covering capability will be lowered. When the average particle diameter is not less than 0.4 μm, the covering capability becomes lower, which is not preferable.

The fine particles of titanium dioxide may be used as they are without being subjected to a surface treatment, but the fine particles of titanium dioxide are preferable to be subjected to the surface treatment with oxides, hydroxides and/or hydrous oxides of one or more metal elements selected from silicon, aluminum, zinc, or iron, before they are deposited on a scale-like base material. As for the fine particles of titanium dioxide as described above, it is preferable to use, for instance, Tipaque™ CR-50 (a $TiO_2$ powder treated with an aluminum compound) produced by Ishihara Sangyo KK or SYMPHO-LIGHT™ WW (a $TiO_2$ powder treated with an aluminum compound and a silicon compound) produced by JGC Catalysts and Chemicals Ltd.

The fine particles of titanium dioxide are used with deposition on a surface of a scale-like base material. The group of such particles is not always required to be present on the entire surface of the scale-like base material, and may be present only in some portions of the surface. However, the group of the particles is preferable to be present homogeneously and sparsely on the surface of the scale-like base material, without being omnipresent on some portions of the surface. Furthermore, the group of the particles is preferable to be present in the monolayer state on the surface of the scale-like base material, without being in the overlaid state.

The multi-functional composite powder contains the fine particles of titanium dioxide deposited on a surface of the scale-like base material, preferably in the range from 5 to 30% by weight. When the content is not more than 5% by weight, it becomes difficult to obtain the appropriate covering capability or the soft-focusing effect. When the content is not less than 30% by weight, the unsmoothness or squeakiness as described above, caused by the fine particles of titanium dioxide becomes stronger, and also the adhesiveness to and the extendability on a human skin become lower, which is not preferable.

The composite oxide containing titanium and iron, which constitutes a thin film on the surface of the scale-like base material on which the group of the above particles has been deposited, is expressed by the general formula (I) below, and can provide the high ultraviolet protective effect since it contains iron therein.

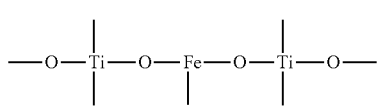

(I)

The multi-functional composite powder contains the composite oxide preferably in the range from 10 to 30% by weight. When the content is not more than 10% by weight, it is difficult to obtain the sufficient ultraviolet protective effect. When the content is not less than 30% by weight, the adhesiveness to and the extendability on a human skin become lower.

The composite oxide contains titanium and iron at a weight ratio ($Fe_2O_3/TiO_2$) being preferably in the range from 0.01 to 0.3, when the titanium is represented as $TiO_2$ and the iron is represented as $Fe_2O_3$. When the weight ratio is not more than 0.01, the color tone of the obtained composite powder is too light or pale, and therefore the effect of suppressing the above white masking becomes lower. When the weight ratio is not less than 0.3, the color tone is too dark or heavy, and therefore it becomes difficult to blend the composite powder with a thin film formed by such a composite oxide, into the cosmetics requesting some light colors.

When the thin film is formed with the composite oxide, it is preferable that the fine particles of titanium dioxide deposited on the surface of the scale-like base material are not completely covered with the composite oxide as shown in FIG. 1 which indicates the conceptual cross-sectional view. Namely, the thickness of the thin film is preferable to be smaller than the average diameter of the fine particles of titanium dioxide. When the composite oxide completely covers the fine particles of titanium dioxide, the functions to be provided by such particles are substantially decreased, which is not preferable. So long as the fine particles of titanium dioxide is not completely covered with the composite oxide, it is acceptable that the surface of the fine particles of titanium dioxide may be slightly covered with the composite oxide.

It is difficult to exactly measure a thickness of the thin film covered with the composite oxide, but from a view point of a weight of the thin film, the thickness is preferably 40 nm or below, and more preferably in the range from 5 to 25 nm.

[Composite Powder 2]

The second multi-functional composite powder to be used in the present invention is constituted by a scale-like base material, a group of particles comprising at least fine particles of titanium dioxide and fine particles of ferric oxide deposited on a surface of the scale-like base material, and a thin film of a composite oxide containing titanium and iron coated thereon.

As for the fine particles of ferric oxide to be used in this case, any material as expressed by the chemical formula of $Fe_2O_3$, which can be used as a color pigment for cosmetics and has a red-brown color, may be used without any specific restriction.

However, an average particle diameter of the fine particles of ferric oxide is preferably in the range from 0.1 to 1.0 μm, and more preferably in the range from 0.2 to 0.6 μm. (When the shape of the fine particles as described above is slender, the average particle diameter (A) is calculated with use of the formula "A=(L+D)/2" in which L represents a major axis of the particle and D represents a minor axis thereof.) When the average particle diameter is not more than 0.1 μm, a coloring effect becomes lower or dull, which makes it impossible to obtain a desired color such as a reddish color. When the average particle diameter is not less than 1.0 μm, a lively color or a bright color is not obtained, although a dark color is obtained, which is not preferable.

The fine particles of ferric oxide may be used as they are without being subjected to a surface treatment like in the case of the fine particles of titanium dioxide as described above, but the fine particles are preferable to be subjected to the surface treatment with oxides, hydroxides and/or hydrous oxides of one or more metal elements selected from silicon, aluminum, zinc, and iron, before they are deposited on a scale-like base material. As for the fine particles of ferric oxide, it is possible to use, for instance, TAROX™ R-516P (a $Fe_2O_3$ powder untreated) produced by Titan Kogyo KK or SYMPHOLIGHT™ RW (a $Fe_2O_3$ powder treated with a silicon compound) produced by JGC Catalysts and Chemicals Ltd.

The group of the particles as described above contains the fine particles of ferric oxide preferably in the range from 0.01 to 10% by weight. When the content is not more than 0.01% by weight, addition of the fine particles becomes insignificant or meaningless. When the content is not less than 10% by weight, a color tone of the obtained composite powder becomes more reddish, and it becomes difficult to blend such a composite powder into the cosmetics requesting some light colors.

Other constituents of the multi-functional composite powder are the same as those described in the Composite Powder 1 above, and therefore description thereof is omitted.

[Preparing Method for the Composite Powder]

A method of preparing the multi-functional composite powder to be used in the present invention is described below in detail, but the present invention is not limited to this method.

Particle Deposition onto the Scale-Like Base Material

Any of the known methods as described below may be used for depositing a group of particles comprising the fine particles of titanium dioxide, or the fine particles of titanium dioxide and the fine particles of ferric oxide on a surface of the scale-like base material.

(1) A method in which a colloidal solution prepared by dispersing the group of particles in a dispersion medium such as water, alcohol, or a mixture thereof is added and dispersed in a suspension of the scale-like base material (which is generally an aqueous suspension) under agitation, then the group of particles is deposited on a surface of the scale-like base material by an electrostatic interaction between both materials, and then the dispersion medium is separated and the obtained solid materials are dried. Then, the dried materials are pulverized or milled with a mortar, an atomizer, a mixer, or the like to make a dried powder thereof.

(2) A method in which a colloidal solution prepared by dispersing the group of particles in a dispersion medium such as water, alcohol, or a mixture thereof is added and dispersed in a suspension of the scale-like base material (which is generally an aqueous suspension) under agitation, and the dispersion liquid is sprayed for drying into a hot air stream of a spray drier. In this method, a concentration of solid materials contained in the dispersion liquid is in the range from 5 to 50% by weight, preferably from 10 to 30% by weight. Furthermore, a temperature of the hot air stream of the spray drier (at an entrance) is preferably in the range from 60 to 130° C.

In the spray-dried powder obtained as described above (namely, a scale-like base material on which the group of particles has been deposited), some powder may be adhered to each other and be aggregated. In this case, the spray-dried powder containing some aggregated ones is preferable to be pulverized or milled with a mortar, an atomizer, a mixer, or the like according to the necessity.

Coating onto the Dried Powder

Any of the known methods as described below can be used for coating on a surface of the dried powder obtained from the above stage, with a titanium compound and a ferric compound for forming a composite oxide containing titanium and iron thereon.

(1) A method in which an aqueous solution of titanium chloride and an aqueous solution of ferric chloride are added in a suspension prepared by suspending the above dried powder in a dispersion medium such as water, alcohol, or a mixture thereof, and the resultant mixture is agitated to coat the surface of the dried powder with a titanium compound and a ferric compound. Then, the solid materials contained in the suspension liquid are separated and dried, and the dried materials thus obtained, after having been pulverized or milled, are calcined at a temperature in the range from 400 to 900° C., by which a multi-functional composite powder coated by a composite oxide containing titanium and iron thereon is obtained.

(2) A method in which a colloidal solution containing a hydroxide of titanium and a hydroxide of iron is added in a suspension prepared by suspending the above dried powder in a dispersion medium such as water, alcohol, or a mixture thereof, and the resultant mixture is agitated, then the dispersion liquid is sprayed into a hot air stream of a spray drier to coat the surface of the dried powder with the metal hydroxide and to dry it at the same time. Thereafter, the dried materials thus obtained, after having been pulverized or milled, are further dried at a temperature in the range from 105 to 150° C.; and then are calcined at a temperature in the range from 400 to 900° C., by which a multi-functional composite powder coated by a composite oxide containing titanium and iron thereon is obtained. In this case, the conditions for drying with a spray drier are the same as those employed in the above method for the "Particle Deposition onto the Scale-like Base Material".

The multi-functional composite powder to be used in the present invention can be prepared by any of the known methods as described above. However, it is preferable that the composite powder is prepared by taking the following matters into consideration.

a) An average particle diameter of the fine particles of titanium dioxide and an amount of the fine particles of titanium dioxide to be deposited on a scale-like base material are adjusted to give an appropriate covering capability as described above.

b) An amount of the composite oxide to be coated on a scale-like base material is adjusted to give an excellent ultraviolet protective effect as described above Furthermore, a thickness of the thin film as described above is adjusted, so that the functions based on the fine particles of titanium dioxide are not concealed or hided by the film.

c) An amount of iron contained in the composite oxide is adjusted to give a function of suppressing the white masking as described above and also to give a yellowish color to the composite powder. Furthermore, an amount of fine particles of ferric oxide to be contained in the group of the particles is adjusted to give a reddish color to the composite powder.

d) An amount of the metal compounds to be mixed with the above dried powder (with fine particles deposited on a scale-like base material) for forming the composite oxide as described above is adjusted, so that an appropriate glossy effect is given to the make-up cosmetics. Furthermore, some other factors are adjusted so as to obtain an appropriate adhesiveness to and a homogeneous cosmetic film on a human skin.

[Cosmetics]

The cosmetics, especially make-up cosmetics according to the present invention are described below in detail.

The cosmetics according to the present invention are obtained by blending the multi-functional composite powder (such as the composite powder A and/or the composite powder B as described above) with various cosmetic ingredients as described below.

An amount of the composite powder to be blended in the cosmetics according to the present invention varies dependent upon a type of cosmetics to be prepared or cosmetic ingredients to be blended, and the content of the composite powder is preferably in the range from 5 to 60% by weight, more preferably in the range from 10 to 50% by weight against the total weight of the cosmetics. When the content is not more than 1% by weight, the basic properties of the composite powder will not fully be realized due to influences by other cosmetic ingredients. When the content is not less than 60% by weight, there is no room for blending an oily liquid or water, or a feeling-improving agent (for instance, inorganic materials such as spherical silica or various types of organic resins), which disadvantageously makes it impossible to produce cosmetic products.

The cosmetic ingredients include, but not limited to, oils and fats such as olive oil, rape seed oil, and beef tallow; waxes such as jojoba oil, carnauba wax, candelilla wax, and beeswax; hydrocarbons such as paraffin, squalane (including synthetic squalane and botanical squalane), α-olefin oligomer, microcrystalline wax, pentane, and hexane; fatty acids such as stearic acid, myristic acid, oleic acid, and α-hydroxy acid; alcohols such as isostearil alcohol, octyl dodecanol, lauryl alcohol, ethanol, isopropanol, butyl alcohol, myristic alcohol, cetanol, stearic alcohol, and behenyl alcohol; alkyl glyceryl ethers; esters such as isopropyl myristate, isopropyl palmitate, ethyl stearate, ethyl oleate, cetyl laurate, decyl oleate; polyalcohols such as ethylene glycol, triethylene glycol, polyethylene glycol, propylene glycol, glycerin, and diglycerin; sugars such as sorbitol, glucose, sucrose, and trehalose; silicon oils such as methyl polysiloxane, methyl hydrogen polysiloxane, methylphenyl silicone oil, various types of denatured silicone oils, and cyclic dimethyl silicone oil; silicon gel bridged with silicon-based and/or other organic compounds; various types of surface-active agent such as nonionic, cationic, anionic, or amphoteric materials; fluorinated oils like perfluoropolyether; various types of polymer such as acacia, carrageenan, agar, xanthan gum, gelatin, alginic acid, guar gum, albumin, pullulan, carboxy vinyl polymer, cellulose or derivatives thereof, polyacrylamide, sodium polyacrylate, and polyvinyl alcohol; anionic, cationic, and nonionic surface-active agents; extracts from animals or plants; amino acids and peptides; vitamins; various types of ultraviolet ray protecting agents such as cynnamic acid derivatives like 2-ethylhexyl 4-methoxycinnamate, salicylic acid derivatives, benzoic ester derivatives, urocanic acid derivatives, or benzophenone derivatives; pesticides or antiseptics; antioxidants; denatured or natural clay minerals; solvents such as butyl acetate, acetone, and toluene; titanium dioxide, zinc oxide, aluminum oxide, aluminum hydroxide, ferric oxide (red iron oxide), hydrated ferric oxide (yellow iron oxide), ferrous ferric oxide (black iron oxide), ceric oxide, zirconium oxide, silica, mica, talc, sericite, boron nitride, barium sulfate, titanated mica having pearl-like gloss, and composites thereof having various particle diameters and particle diameter distribution; various types of organic pigments and colorants; water, and aroma chemicals.

The inorganic compounds such as aluminum oxide or zinc oxide as described above may be subjected to a surface treatment with silicon, fluorine compound, metallic soap or the like, before blending in cosmetics.

Furthermore, the cosmetics may contain resin particles such as poly methyl methacrylate, nylon, silicone resin, silicone rubber, polyethylene, polyester, and polyurethane.

Furthermore, as an ingredient providing the whitening effectiveness, the cosmetics may contain any of arbutin, Koji acid, vitamin C, sodium ascorbate, magnesium ascorbyl phosphate, ascorbyl dipalmitate, ascorbyl glucoside, and other ascorbic acid derivatives, placental extract, sulfur, botanical extracts such as oil-soluble glycyrrhiza extract or mulberry bark extract, linoleic acid, linolenic acid, lactic acid, and tranexamic acid.

Furthermore, the cosmetics may contain, as an ingredient capable of improving a rough and dry skin, any of vitamin C, any of ingredients having the anti-aging effect such as carotinoids, flavonoid, tannin, coffee derivatives, lignan, saponin, letinoic acid and other chemicals structurally similar to letinoic acid, N-acetyl glucosamine, and α-hydroxylic acid; polyalcohols such as glycerin, propylene glycol, 1,3-butylene glycol; sugars such as mixed isomerized sugars, trehalose, and pullulan; biomacromolecules such as sodium hyaluronate, collagen, elastin, chitin chitosan, and sodium chondroitin sulfate, amino acids, betaine, ceramide, sphingolipids, cholesterol or derivatives thereof, ε-aminated pronic acid, glycyrrhizinic acid, and various types of vitamins.

Furthermore, it is allowable to use, without any specific restriction, any of cosmetic ingredients listed in Standard for Raw Materials of Medicated Cosmetics 2006 (issued by YAKUJI NIPPOU KK, Jun. 16, 2006) or in International Cosmetic Ingredient Dictionary and Handbook (issued by The Cosmetic, Toiletry, and Fragrance Association, Eleventh Edition 2006).

However, it is preferable that the cosmetic ingredients are selected by taking the following matters into consideration. Namely, although the fine particles of titanium dioxide (as a white pigment) are generally blended in cosmetics such as make-up cosmetics for improving the covering capability or other functions, it is not preferable to blend such fine particles of titanium dioxide in the cosmetics together with the multi-functional composite powder used in the present invention. When the fine particles of titanium dioxide are added in addition to the multi-functional composite powder, the effect of the composite powder for suppressing a white masking becomes lower, and sometimes a homogeneous cosmetic film is not formed on a human skin.

The cosmetics produced by the above method are used in various forms such as powder-like, cake-like, pencil-like, stick-like, gel-like, mousse-like, liquid-like, and cream-like states. More specifically, the cosmetics can be used as base make-up cosmetics such as powder foundation, liquid foundation, oily foundation, mousse foundation, and pressed powder; point make-up cosmetics such as eye shadow, eyebrow; eye liner, mascara, and lip stick; body powder; milky lotion; cream; make-up base; cosmetics for cleaning such as soap, cleansing foam, and creams for removing make-up cosmetics; skin care cosmetics such as those for moistening and prevention of rough dry skin, for caring horny layer, for massage, for caring wrinkles or skin surface waviness, for caring damages caused by UV rays, for whitening, and for anti-oxidation; hair-care cosmetics such as those for hair growth, for prevention of scurf, for prevention of itch, for cleaning for conditioning or styling, for permanent wave, for coloring or bleaching hairs; body-care cosmetics such as those for cleaning, for sun screening, for skin-care, for slimming, for improving blood circulation, for suppressing itch, for prevention of body odor, for controlling perspiration, for caring body hairs, and for repelling water; fragrant cosmetics such as perfumes, eau de parfum, eau de toilette, cologne, shower cologne, wet perfume, body lotion, and bath oil; and oral care cosmetics such as those for teeth-brushing and mouth-washing. Of these applications as described above, it is especially preferable to use the cosmetics according to the present invention as make-up cosmetics such as powder foundations, liquid foundations, and pressed powder.

The cosmetics obtained as described above can provide the basic properties as described above, namely a) an excellent adhesiveness, b) an excellent extendability, c) an appropriate glossy effect, d) a homogeneous cosmetic film, e) an appropriate covering capability, f) a cosmetic film not causing a white masking, g) a high compatibility between a color appearance of cosmetics and a color tone of the cosmetic film, h) an excellent soft-focusing capability, i) an excellent ultra-violet protective effect, and the like.

The multi-functional composite powder to be used in the present invention can be blended in other cosmetic products. However, since these cosmetic products are not always required to satisfy all of the basic properties as described above, the composite powder should preferably be used according to the necessity.

[Measuring Method]

The measuring method employed in embodiments of the present invention is described below in detail.

(1) Average Particle Diameter of a Scale-Like Base Material

A sample of the scale-like base material was measured with a particle size measuring device based on the laser diffraction and scattering system (produced by HORIBA SEI-SAKUSHO KK., LA-300) to obtain an average value of the particle diameter.

(2) Thickness of a Scale-Like Base Material 100 particles selected from a sample of the scale-like base material were photographed with a scan electron microscope (produced by Hitachi, Ltd., S-5200N) to obtain an average value of the thickness.

(3) Average Particle Diameter of the Fine Particles of Titanium Dioxide 100 particles selected from a sample of the fine particles of titanium dioxide were photographed with a scan electron microscope (produced by Hitachi, Ltd., S-5200N) to obtain an average value of the particle diameter.

(4) Average Particle Diameter of the Fine Particles of Ferric Oxide 100 particles selected from a sample of the fine particles of ferric oxide were photographed with a scan electron microscope (produced by Hitachi, Ltd., S-5200N) to obtain an average value of the particle diameter. In this case, as the shape of the fine particles of ferric oxide used in the present invention was almost slender, the average particle diameter (A) was calculated with use of the formula "$A=(L+D)/2$" in which L represents a major axis of the particle and D represents a minor axis thereof.

EXAMPLES

The present invention is described in further details below with reference to examples. However, it should be noted that the present invention is not limited to these embodiments.

Preparation of Composite Powder

Example of Preparation 1

244 g of mica with the average particle diameter of 9 μm (produced by YAMAGUCHI UNMO K.K, Y-1800) as a scale-like base material was added to 1200 ml of pure water and the mixture solution was fully agitated, and then the pH of the mixture solution was adjusted to about 2.3 by adding an aqueous solution of hydrogen chloride with the concentration of 10% by weight under agitation to obtain a suspension (namely, a liquid in which scale-like base materials were suspended).

Then, 57 g of fine particles of titanium dioxide with the average diameter of 0.25 μm (produced by Ishihara Sangyo KK.: Tipaque™ CR-50) was added to the above suspension and the suspension was heated to the temperature of 60° C. under agitation. Then, the pH of the suspension was adjusted to 5.0 by adding an aqueous solution of ammonia with the concentration of 15% by weight, and 120 ml of an aqueous solution of calcium chloride with the concentration of 5% by weight as a flocculating agent was further added to the suspension, and then the mixture solution was agitated for 30 minutes.

Then, the mixture solution was cooled down to the room temperature. Thereafter, solid materials were filtered from the mixture solution, and washed with pure water, and then were dried for 16 hours at the temperature of 110° C.

Furthermore, blocks of the obtained dried materials were put in a mixer and pulverized or milled, and 300 g of the dried powder was obtained, the particle of which is constituted by mica as a scale-like base material and fine particles of titanium dioxide deposited on the base material of mica.

280 g of the dried powder as described above was added and suspended into 1200 ml of pure water, and the suspension was fully agitated. Then, the pH of the suspension was adjusted to about 5.5 by adding an aqueous solution of hydrogen chloride with the concentration of 10% by weight and was further heated to the temperature of 60° C. under agitation to obtain a suspension (namely, a liquid in which the above dried powders were suspended).

Then, 35 g of an aqueous solution of ferric chloride with the concentration of 10% by weight and 665 g of an aqueous solution of titanium chloride with the concentration of 10% by weight were mixed with each other. The mixture solution was added to the above suspension over 17 hours under agitation and then was cooled down to the room temperature. When the mixture solution was added to the suspension, the pH of the suspension was kept at 5.5 by adding an ammonia water with the concentration of 15% by weight.

The solid materials contained in the suspension as described above were filtered, and were washed with pure water, and then were dried for 16 hours at the temperature of 110° C. Thereafter, the dried materials thus obtained were pulverized in a mixer, and then were calcined for 3 hours at the temperature of 800° C. to obtain a multi-functional composite powder A constituted by mica, fine particles of titanium, dioxide deposited on the mica and a thin film of a composite oxide containing titanium and iron coated thereon (hereinafter referred to as "the composite powder A").

Example of Preparation 2

Multi-functional composite powders B to F, H to J (hereinafter referred to as "the composite powders B to F" and "the composite powders H to J") were obtained in accordance with the preparing method as described in Example of Preparation 1 above, but the amounts of mica and fine particles of titanium dioxide to be added, the amounts of ferric chloride (in terms of $Fe_2O_3$) and titanium chloride (in terms of TiO2) to be added, and also the mixing ratio ($Fe_2O_3/TiO_2$) between the ferric chloride and the titanium chloride, which are all on the weight basis, were changed as shown in Table 1.

Example of Preparation 3

Composite powder K coated with a composite oxide containing titanium and iron (hereinafter referred to as "the composite powder K") was obtained in accordance with the preparing method as described in Example of Preparation 1 above, but the fine particles of titanium dioxide were not deposited on mica, and also the amounts of mica, ferric chloride (in terms of $Fe_2O_3$) and titanium chloride (in terms of $TiO_2$) to be added, which are all on the weight basis, were changed as shown in Table 1.

Example of Preparation 4

Composite powder L coated with titanium dioxide based on titanium chloride (hereinafter referred to as "the composite powder L") was obtained in accordance with the preparing method as described in Example of Preparation 1 above, but the aqueous solution of ferric chloride was not added, and also the amounts of mica, fine particles of titanium dioxide and titanium chloride (in terms of $TiO_2$) to be added, which are all on the weight basis, were changed as shown in Table 1.

Example of Preparation 5

Composite powder M coated with ferric oxide based on ferric chloride (hereinafter referred to as "the composite powder M") was obtained in accordance with the preparing method as described in Example of Preparation 1 above, but the aqueous solution of titanium chloride was not added, and also the amounts of mica, fine particles of titanium dioxide and ferric chloride (in terms of $Fe_2O_3$) to be added, which are all on the weight basis, were changed as shown in Table 1.

Example of Preparation 6

244 g of mica with the average diameter of 9 μm (YAMAGUCHI UNMO KK: Y-1800) as a scale-like base material was added to 1200 ml of pure water and the mixture solution was fully agitated, and then the pH of the mixture solution was adjusted to about 2.3 by adding an aqueous solution of hydrogen chloride with the concentration of 10% by weight under agitation to obtain a suspension (namely, a liquid in which scale-like base materials were suspended).

Then, 53 g of fine particles of titanium dioxide with the average particle diameter of 0.25 μm (produced by Ishihara Sangyo KK.: Tipaque™ CR-50) and 4 g of fine particles of ferric oxide with the average particle diameter of 0.45 μm (produced by Titan Kogyo KK: TAROX™ R-516P) were added to the above suspension, and the suspension was heated to 60° C. under agitation. Then, the pH of the suspension was adjusted to 5.0 by adding an ammonia water with the concentration of 15% by weight, and 120 ml of an aqueous solution of calcium chloride with the concentration of 5% by weight as a flocculating agent was added to the suspension, and then the mixture solution was agitated for 30 minutes.

Then, the mixture solution was cooled down to the room temperature. Thereafter, solid materials were filtered from the mixture solution, and washed with pure water, and then were dried for 16 hours at the temperature of 110° C.

Furthermore, blocks of the obtained dried materials were put in a mixer and pulverized or milled, and 300 g of the dried powder was obtained, the particle of which is constituted by mica as a scale-like base material, and fine particles of titanium dioxide and fine particles of ferric oxide deposited on the base material of mica.

280 g of the dried powder as described above was added and suspended into 1200 ml of pure water, and the suspension was fully agitated. Then, the pH of the suspension was adjusted to about 5.5 by adding an aqueous solution of hydrogen chloride with the concentration of 10% by weight and was further heated to the temperature of 60° C. under agitation to obtain a suspension (namely, a liquid in which the above dried powders were suspended).

Then, 35 g of an aqueous solution of ferric chloride with the concentration of 10% by weight and 665 g of an aqueous solution of titanium chloride with the concentration of 10% by weight were mixed with each other. The mixture solution was added to the above suspension over 17 hours under agitation, and then was cooled down to the room temperature. When the mixture solution was added to the suspension, the pH of the suspension was kept at 5.5 by adding an ammonia water with the concentration of 15% by weight.

The solid materials contained in the suspension as described above were filtered, and were washed with pure water, and then were dried for 16 hours at the temperature of 110° C. Thereafter, the dried materials thus obtained were pulverized in a mixer, and then were calcined for 3 hours at the temperature of 800° C. to obtain a multi-functional composite powder G constituted by mica, and fine particles of titanium dioxide and also fine particles of ferric oxide deposited on the mica, and a thin film of a composite oxide containing titanium and iron coated thereon (hereinafter referred to as "the composite powder G").

Preparation of Mixed Powder

Example of Preparation 7

65 g of mica with the average particle diameter of 9 μm (YAMAGUCHI UNMO KK.: Y-1800) as a scale-like material, 15 g of fine particles of titanium dioxide with the average particle diameter of 0.25 μm (produced by Ishihara Sangyo KK.: Tipaque™ CR-50), and 20 g of nanoparticles of titanium dioxide with the average particle diameter of 35 nm (produced by TAYCA CORPORATION: MT-500B) were put in a mixer, and were fully mixed to obtain a mixed powder N containing mica, fine particles of titanium dioxide, and nanoparticles of titanium dioxide.

TABLE 1

| | Preparation of the composite powder or the mixed powder (Wt %) | | | | | | | |
|---|---|---|---|---|---|---|---|---|
| | | Color pigments deposited on the scale-like base material or mixed | | | Components for forming the thin film (composite oxide) and the weight ratio of $Fe_2O_3/TiO_2$ in the composite oxide | | | |
| Composite powder | Scale-like base material Mica | Fine particles of titanium oxide | Fine particles of ferric oxide | Nano particles of titanium oxide | Ferric chloride (As $Fe_2O_3$) | Titanium chloride (As $TiO_2$) | Sum of ferric chloride and titanium chloride | Weight ratio of $Fe_2O_3/TiO_2$ to be mixed |
| A | 65 | 15 | — | — | 1 | 19 | 20 | 0.053 |
| B | 50 | 30 | — | — | 1 | 19 | 20 | 0.053 |
| C | 75 | 5 | — | — | 1 | 19 | 20 | 0.053 |
| D | 75 | 15 | — | — | 1 | 9 | 10 | 0.111 |
| E | 55 | 15 | — | — | 1 | 29 | 30 | 0.034 |
| F | 72 | 15 | — | — | 3 | 10 | 13 | 0.300 |
| G | 65 | 14 | 1 | — | 1 | 19 | 20 | 0.053 |
| H | 45 | 35 | — | — | 1 | 19 | 20 | 0.053 |
| I | 80 | 15 | — | — | 1 | 4 | 5 | 0.250 |
| J | 45 | 15 | — | — | 1 | 39 | 40 | 0.025 |

TABLE 1-continued

Preparation of the composite powder or the mixed powder (Wt %)

| Composite powder | Scale-like base material Mica | Color pigments deposited on the scale-like base material or mixed | | | Components for forming the thin film (composite oxide) and the weight ratio of $Fe_2O_3/TiO_2$ in the composite oxide | | | |
|---|---|---|---|---|---|---|---|---|
| | | Fine particles of titanium oxide | Fine particles of ferric oxide | Nano particles of titanium oxide | Ferric chloride (As $Fe_2O_3$) | Titanium chloride (As $TiO_2$) | Sum of ferric chloride and titanium chloride | Weight ratio of $Fe_2O_3/TiO_2$ to be mixed |
| K | 80 | 0 | — | — | 1 | 19 | 20 | 0.053 |
| L | 65 | 15 | — | — | 0 | 20 | 20 | Only $TiO_2$ |
| M | 84 | 15 | — | — | 1 | 0 | 1 | Only $Fe_2O_3$ |
| Mixed powder N | 65 | 15 | — | 20 | — | — | — | — |

Example 1 and Comparative Example 1

Preparation of Powder Foundation

To prepare powder foundations with the blending ratios (on the weight percent basis) as shown in Table 2, a component (1) selected from the composite powders A, B, D to M prepared in Examples of Preparations 1 to 6 and the mixed powder N prepared in Examples of Preparations 7, and other cosmetic components (2) to (8) as shown in Table 2 were put in a mixer, and were fully mixed to make a powder homogeneously mixed. Then, the cosmetic components (9) and (11) as shown in Table 2 were further put in the mixer, and were fully mixed. Thereafter, the obtained cake-like substances were pulverized, and about 12 g of the pulverized substance taken out from each sample, was put in a square metallic plate with the size of 46 mm×54 mm×4 mm. Then, each of the substances was press-molded in the plate.

Through the blending operations as described above, each of the powder foundations as shown in Table 3 was prepared, namely the powder foundations A-(50), D-(50), E-(50), F-(50), H-(50), 1-(50), or J-(50) containing the composite powders A, D, E, F, H, I, or J by the content of 50% by weight respectively (hereinafter referred to as "the example cosmetics 1A-(50), 1D-(50), 1E-(50), 1F-(50), 1H-(50), 1I-(50), or 1J-(50)" respectively); the powder foundations A-(30), B-(30), or G-(30) containing the composite powders A, B, or G by the content of 30% by weight respectively (hereinafter referred to as "the example cosmetics 1A-(30), 1B-(30), or 1G-(30)" respectively); the power foundations K-(50), L-(50), or M-(50) containing the composite powders K, L, or M respectively (hereinafter referred to as "the comparative example cosmetics 1K-(50), 1L-(50), or 1M-(50)" respectively); and the power foundation N-(50) containing the mixed powder N by the content of 50% by weight (hereinafter referred to as "the comparative example cosmetics 1N-(50)").

TABLE 3

| Powder foundation | Composite powder or mixed powder | Content (Wt %) | Example cosmetics | Comparative example cosmetics |
|---|---|---|---|---|
| A-(50) | A | 50 | 1A-(50) | — |
| A-(30) | A | 30 | 1A-(30) | — |
| B-(30) | B | 30 | 1B-(30) | — |
| D-(50) | D | 50 | 1D-(50) | — |
| E-(50) | E | 50 | 1E-(50) | — |
| F-(50) | F | 50 | 1F-(50) | — |
| G-(30) | G | 30 | 1G-(30) | — |
| H-(50) | H | 50 | 1H-(50) | — |
| I-(50) | I | 50 | 1I-(50) | — |
| J-(50) | J | 50 | 1J-(50) | — |
| K-(50) | K | 50 | — | 1K-(50) |
| L-(50) | L | 50 | — | 1L-(50) |
| M-(50) | M | 50 | — | 1M-(50) |
| N-(50) | Mixed powder N | 50 | — | 1N-(50) |

Example 2 and Comparative Example 2

Preparation of Pressed Powder

To prepare pressed powders with the blending ratios (on the weight percent basis) as shown in Table 4, a component (1) selected from the composite powders A and C prepared in Example of Preparation 1 to 2 and the mixed powder N prepared in Example of Preparation 7, and other cosmetic components (2) to (8) as shown in Table 4 were put in a mixer, and were fully mixed to make a powder homogeneously mixed. Then, the cosmetic components (9) and (10) as shown in Table 4 were further put in the mixer, and were fully mixed. Thereafter, the obtained cake-like substances were pulverized, and about 12 g of the pulverized substance taken out from each sample, was put in a square metallic plate with the

TABLE 2

| | Cosmetic constituents for a powder foundation | Content (Wt %) (Composite powders A, D, E, F, H, I, J, K, L, M or mixed powder N blended) | Content (Wt %) (Composite powders A, B or G blended) |
|---|---|---|---|
| (1) | Composite powders A, B, D to M or mixed power N (treated by silicone) | 50.0 | 30.0 |
| (2) | Talc (treated by silicone) | 31.4 | 39.6 |
| (3) | Mica (treated by silicone) | 0.0 | 12.8 |
| (4) | Spherical silica (treated by silicone) | 3.0 | 3.0 |
| (5) | Methyl paraben | 0.2 | 0.2 |
| (6) | Yellow iron oxide | 1.5 | 1.5 |
| (7) | Red iron oxide | 0.5 | 0.5 |
| (8) | Black iron oxide | 0.4 | 0.4 |
| (9) | Fluid paraffin | 3.0 | 3.0 |
| (10) | Dimethycon | 5.0 | 5.0 |
| (11) | Tri 2-ethylhexane glyceryl | 5.0 | 5.0 | size of 46 mm×54 mm×4 mm. Then, each of the substances was press-molded in the plate.

Through the blending operations as described above, the pressed powders as shown in Table 5 were prepared, namely the pressed powder A-(10) containing the composite powder A by the content of 10% by weight (hereinafter referred to as "the example cosmetic 2A-(10)"); the pressed powder C-(50) containing the composite powder C by the content of 50% by weight (hereinafter referred to as "the example cosmetic 2C-(50)"), and the pressed powder N-(10) containing the mixed power N by the content of 10% by weight (hereinafter referred to as "the comparative example cosmetics 2N-(10)").

pared in Comparative example 1, namely the comparative example cosmetics 1K-(50), 1L-(50), 1M-(50), and 1N-(50) in applying these powder foundations on the skin of each monitor. The results of the hearing investigation which was performed in accordance with the following criteria, are shown in Table 6.

⊚: Sense or feeling in use is best.

○: Sense or feeling in use is good.

Δ: Sense or feeling in use is slightly not good.

X: Sense or feeling in use is not good.

TABLE 4

|   | Cosmetic constituents for a pressed powder | Content (Wt %) (Composite powder A blended) | Content (Wt %) (Composite powder C blended) | Content (Wt %) (Mixed powder N blended) |
|---|---|---|---|---|
| (1) | Composite powder A, C, or mixed powder N (treated by silicone) | 10.0 | 50.0 | 10.0 |
| (2) | Talc (treated by silicone) | 54.4 | 29.4 | 54.2 |
| (3) | Mica (treated by silicone) | 15.0 | 0.0 | 15.0 |
| (4) | Kaoline | 10.0 | 10.0 | 10.0 |
| (5) | Zinc mystirate | 5.0 | 5.0 | 5.0 |
| (6) | Methyl paraben | 0.2 | 0.2 | 0.2 |
| (7) | Yellow iron oxide | 0.0 | 0.0 | 0.2 |
| (8) | Red iron oxide | 0.4 | 0.4 | 0.4 |
| (9) | Squaran | 3.0 | 3.0 | 3.0 |
| (10) | Glycerin triisooctanate | 2.0 | 2.0 | 2.0 |

TABLE 5

| Pressed powder | Composite powder or mixed powder | Content (Wt %) | Example cosmetics (Sample No.) | Comparative example cosmetics (Sample No.) |
|---|---|---|---|---|
| A-(10) | Composite powder A | 10 | 2A-(10) | |
| C-(50) | Composite powder C | 50 | 2C-(50) | |
| N-(10) | Mixed powder N | 10 | | 2N-(10) |

Example 3 and Comparative Example 3

Sensory Evaluation of Powder Foundations

A hearing investigation as a sensory evaluation was made from 20 monitors with use of the powder foundations prepared in Example 1, namely the example cosmetics 1A-(50), 1A-(30), 1B-(30), 1D-(50), 1E-(50), 1F-(50), 1G-(30), 1H-(50), 1I-(50) and 1J-(50), and the powder foundations pre- Evaluation of Powder Foundations on Ultraviolet Protective Capability 0.08 g of the substance was taken from each of the powder foundations prepared in Example 1, namely the example cosmetics 1A-(50), 1A-(30), 1B-(30)), 1D-(50), 1E-(50), 1F-(50), 1G-(30), 1H-(50), 1I-(50) and 1J-(50), and each of the powder foundations prepared in Comparative Example 1, namely the comparative example cosmetics 1K-(50), 1L-(50), 1M-(50) and 1N-(50), and then the sample was homogeneously applied onto 40 cm² of a surgical tape (produced by 3M Corp: Transpore tape).

Each of the sample was measured five times to obtain the value of SPF (Sun Protection Factor) indicating a degree of the ultraviolet protective capability with the SPF analyzer (produced by Optometrics Corp: SPF290S, light source: 75 W xenon lamp), and the average value was calculated. The results of the evaluation test, which mean that the larger the SPF value is, the higher the ultraviolet protective capability is, are as shown in Table 7.

TABLE 6

| Results of sensory evaluation test ||||||||||
|---|---|---|---|---|---|---|---|---|---|
| Sample for evaluation || Cosmetics |||||| Compatibility between color ||
| Example cosmetics (Sample No.) | Comparative example cosmetics (Sample No.) | Homogeneous cosmetic film | film not causing white masking | Appropriate covering capability | Appropriate glossy effect | Excellent extendability | Excellent adhesiveness | appearance of cosmetics and color tone of cosmetic film | Soft focusing effect |
| 1A-(50) | — | ⊚ | ⊚ | ⊚ | ⊚ | ○ | ⊚ | ⊚ | ⊚ |
| 1A-(30) | — | ⊚ | ⊚ | ○ | ○ | ○ | ○ | ⊚ | ○ |
| 1B-(30) | — | ⊚ | ⊚ | ○ | ○ | ○ | ○ | ○ | ⊚ |
| 1D-(50) | — | ⊚ | ⊚ | ⊚ | ○ | ⊚ | ○ | ⊚ | ⊚ |
| 1E-(50) | — | ○ | ⊚ | ⊚ | ○ | ○ | ○ | ○ | ⊚ |
| 1F-(50) | — | ⊚ | ⊚ | ⊚ | ○ | ○ | ○ | ⊚ | ⊚ |

TABLE 6-continued

Results of sensory evaluation test

| Sample for evaluation | | Cosmetics | | | | | | Compatibility between color | |
|---|---|---|---|---|---|---|---|---|---|
| Example cosmetics (Sample No.) | Comparative example cosmetics (Sample No.) | Homogeneous cosmetic film | film not causing white masking | Appropriate covering capability | Appropriate glossy effect | Excellent extendability | Excellent adhesiveness | appearance of cosmetics and color tone of cosmetic film | Soft focusing effect |
| 1G-(30) | — | ◉ | ◉ | ◉ | ◉ | ○ | ◉ | ◉ | ○ |
| 1H-(50) | — | Δ | Δ | Δ | Δ | ○ | ○ | Δ | ◉ |
| 1I-(50) | — | ○ | ○ | ◉ | Δ | ◉ | Δ | ○ | ◉ |
| 1J-(50) | — | Δ | ○ | ◉ | Δ | Δ | Δ | ◉ | ◉ |
| — | 1K-(50) | ◉ | ◉ | X | Δ | ○ | ○ | ◉ | X |
| — | 1L-(50) | ○ | X | ◉ | ◉ | ○ | ◉ | ○ | ◉ |
| — | 1M-(50) | X | X | ◉ | X | ○ | X | ○ | ◉ |
| — | 1N-(50) | X | X | ○ | X | X | X | X | X |

TABLE 7

| Sample for evaluation | | Ultraviolet protective capability (SPF value) |
|---|---|---|
| Example cosmetics (Sample No.) | Comparative example cosmetics (Sample No.) | |
| 1A-(50) | — | 40 |
| 1A-(30) | — | 30 |
| 1B-(30) | — | 33 |
| 1D-(50) | — | 20 |
| 1E-(50) | — | 43 |
| 1F-(50) | — | 21 |
| 1G-(30) | — | 40 |
| 1H-(50) | — | 35 |
| 1I-(50) | — | 13 |
| 1J-(50) | — | 46 |
| — | 1K-(50) | 35 |
| — | 1L-(50) | 36 |
| — | 1M-(50) | 11 |
| — | 1N-(50) | 30 |

It was found that, as clearly shown in Table 6, each of the powder foundations containing the composite powders A, B, D to J according to the present invention, namely the example cosmetics 1A-(50), 1A-(30), 1B-(30), 1D-(50), 1E-(50), 1F-(50), 1G-(30), 1H-(50), 1I-(50), and 1J-(50) had no problems in the basic properties required for cosmetics, namely in the properties of (a) an excellent adhesiveness, (b) an excellent extendability, (c) an appropriate glossy effect, (d) a homogeneous cosmetic film, (e) an appropriate covering capability, (f) a cosmetic film not causing a white masking, (g) a high compatibility between a color appearance of cosmetics and a color tone of the cosmetic film, and (h) an excellent soft-focusing capability, and the like. It was further found that, of these foundations as described above, the powder foundations containing the composite powders A, B, D to G according to the present invention, namely the example cosmetics 1A-(50), 1A-(30), 1B-(30), 1D-(50), 1E-(50), 1F-(50), and 1G-(30) were excellent in all of the basic properties.

In a case of the powder foundation containing the composite powder K (prepared by not depositing fine particles of titanium dioxide on mica), namely the comparative example cosmetics 1K-(50), it was found that the covering capability was too low.

Furthermore, in a case of the powder foundation containing the composite powder H (prepared by depositing a relatively large amount of the fine particles of titanium dioxide on mica), namely the example cosmetics 1H-(50), it was found that the covering capability was rather too high, and other functions as described above were somewhat lower than those for other example cosmetics. Accordingly, it is preferable that the composite powder to be used in the present invention contains fine particles of titanium dioxide deposited on a scale-like base material such as mica, in the range from 5 to 30% by weight.

Furthermore, in a case of the powder foundation containing the composite powder G (prepared by depositing fine particles of titanium dioxide and also fine particles of ferric oxide on mica), namely the example cosmetic 1G-(50), it was found that, when the powder foundation was applied on the facial skin of the monitors, the effect of suppressing the white masking became higher than those for other example cosmetics in which the composite powder not containing fine particles of ferric oxide deposited on mica was blended.

It was further found that, as clearly shown in Table 7, each of the powder foundations containing the composite powders A, B, D to J according to the present invention, namely the example cosmetics 1A-(50), 1B-(30), 1D-(50), 1E-(50), 1F-(50), 1G-(30), 1H-(50), 1I-(50), and 1J-(50) had no problem in the ultraviolet protective capability. Furthermore, it was found that, of these foundations as described above, the powder foundations containing the composite powders A, B, E, G, H, and J respectively, namely the example cosmetics 1A-(50), 1A-(30), 1B-(30), 1E-(50), 1G-(30), 1H-(50), and 1J-(50) were especially excellent in the ultraviolet protective capability.

It was further found that, in a case of the powder foundation containing the composite powder D, F, or I (prepared by coating thereon a relatively small amount of the composite oxide, especially in a content of titanium), namely the example cosmetics 1D-(50), 1F-(50), or 1I-(50), the extendability on a cosmetic film was excellent, but the adhesiveness to a human skin was not so excellent and the ultraviolet protective capability was somewhat lower. Furthermore, in a case of the powder foundation containing the composite powder J (prepared by coating thereon a relatively large amount of the composite oxide, especially in a content of titanium), namely the example cosmetic 1J-(50), it was found that the adhesiveness to a human skin and the ultraviolet protective capability were excellent, but the cosmetic film was somewhat lower in the extendability. Accordingly, it is preferable that the composite powder to be used in the present invention contains a thin film of the composite oxide coated thereon, in the range from 10 to 30% by weight.

It was further found that, in a case of the powder foundation containing the composite powder L (prepared by coating thereon only with titanium dioxide and with no addition of iron compound), namely the comparative example cosmetics 1L-(50), the white masking was occurred in the cosmetic film. Furthermore, it was found that the powder foundation containing the composite powder M (prepared by coating thereon only with ferric oxide and with no addition of titanium compound), namely the comparative example cosmetics 1M-(50) was inferior in many of the basic properties as described above. Accordingly, it is preferable that the composite powder is coated with a composite oxide containing titanium and iron, and also the weight ratio of $Fe_2O_3/TiO_2$ in the composite oxide is preferably in the range from 0.01 to 0.3, when the titanium is represented as $TiO_2$ and the iron is represented as $Fe_2O_3$.

Furthermore, it was found that the powder foundation containing the mixed powder N, namely the comparative example cosmetic 1N-(50) was excellent in the ultraviolet protective capability, but was inferior in many of other basic properties as described above.

Example 4 and Comparative Example 4

Sensory Evaluation of Pressed Powders

A hearing investigation as a sensory evaluation was made from 20 monitors with use of the pressed powders prepared in Example 2, namely the example cosmetics 2A-(10) and 2C-(50), and the pressed powder prepared in Comparative Example 2, namely the comparative example cosmetics 2N-(10) in applying these pressed powders on the skin of each monitor. The results of the hearing investigation which was performed in accordance with the following criteria, are shown in Table 8.

⊚: Sense or feeling in use is best.
○: Sense or feeling in use is good.
Δ: Sense or feeling in use is slightly not good.
X: Sense or feeling in use is not good.

DESCRIPTION OF MARKED FIGURES

1: Scale-like base material such as mica.
2: Fine particles of titanium dioxide.
3: Thin film of a composite oxide containing titanium and iron.

The invention claimed is:

1. A cosmetic composition containing a multi-functional composite powder wherein the multifunctional composite powder is constituted by:
   (i) a scale-like base material,
   (ii) a group of particles disposed on and covering only a part of a surface of the scale-like base material, the group of particles comprising at least particles of titanium dioxide having an average particle diameter of from 0.1 to 0.4 μm, and
   (iii) a thin film of a composite oxide of titanium and iron on and coating a part of the surface of the scale-like base material, wherein
      the thin film of the composite oxide of titanium and iron coats the part of the surface of the scale-like base material that is not covered by the group of particles,
      the thin film has a thickness smaller than the average diameter of the particles of the group of particles, and
      the particles of the group of particles are not completely covered by the thin film so that visible light incident on the particles is scattered.

2. The cosmetic composition according to claim 1, wherein the group of particles further includes particles of ferric oxide

TABLE 8

| | | Results of sensory evaluation test | | | | | | | |
|---|---|---|---|---|---|---|---|---|---|
| Sample for evaluation | | | | | | | | Compatibility | |
| Example cosmetics (Sample No.) | Comparative example cosmetics (Sample No.) | Homogeneous cosmetic film | Cosmetic film not causing white masking | Appropriate covering capability | Appropriate glossy effect | Excellent extendability | Excellent adhesiveness | between color appearance of cosmetics and color tone of cosmetic film | Soft focusing effect |
| 2A-(10) | | ○ | ⊚ | ○ | ⊚ | ⊚ | ○ | ⊚ | ○ |
| 2C-(50) | | ○ | ⊚ | ⊚ | ○ | ○ | ⊚ | ⊚ | ○ |
| | 2N-(10) | Δ | X | ○ | ○ | X | Δ | X | X |

It was found that, as clearly shown in Table 8, the pressed powders containing the composite powder A or C according to the present invention, namely the example cosmetics 2A-(10) and 2C-(50) were excellent in all of the basic properties as described above, namely in the properties of (a) an excellent adhesiveness, (b) an excellent extendability, (c) an appropriate glossy effect, (d) a homogeneous cosmetic film, (e) an appropriate covering capability, (f) a cosmetic film not causing a white masking, (g) a high compatibility between a color appearance of cosmetics and a color tone of the cosmetic film, and (h) an excellent soft-focusing capability.

On the other hand, it was found that the pressed powder containing the mixed powder N, namely the comparative example cosmetics 2N-(10) was inferior in many of the basic properties as described above.

BRIEF DESCRIPTION OF THE DRAWINGS

FIG. 1 is a view showing a conceptual cross section of the composite powder according to the present invention.

in an amount from 0.01 to 10.0% by weight of the group of particles, the particles of ferric oxide having an average particle diameter of from 0.1 to 1.0 μm.

3. The cosmetic composition according to claim 1, wherein the particles of titanium dioxide have a white color and are a color pigment.

4. The cosmetic composition according to claim 2, wherein the particles of ferric oxide have a red-brown color and are a color pigment.

5. The cosmetic composition according to claim 1, wherein the particles of titanium dioxide have been subjected to a surface treatment with oxides, hydroxides, and/or hydrous oxides of one or more metal elements selected from the group consisting of silicon, aluminum, zinc, and iron.

6. The cosmetic composition according to claim 1, wherein the particles of titanium dioxide disposed on part of the surface of the scale-like base material are present in an amount from 5 to 30% by weight of the multi-functional composite powder.

7. The cosmetic composition according to claim 1, wherein the thin film of the composite oxide is present in an amount from 10 to 30% by weight of the multi-functional composite powder.

8. The cosmetic composition according to claim 1, wherein the composite oxide of titanium and iron contains titanium and iron in a weight ratio ($Fe_2O_3/TiO_2$) in a range from 0.01 to 0.3, when the titanium is represented as $TiO_2$ and the iron is represented as $Fe_2O_3$.

9. The cosmetic composition according to claim 1, wherein the multi-functional composite powder is present in an amount from 5 to 60% by weight of the cosmetic composition.

10. The cosmetic composition according to claim 1, wherein the cosmetic composition does not contain particles of titanium dioxide as a pigment other than in the multi-functional composite powder.

11. The cosmetic composition according to claim 1, wherein the cosmetic composition is a make-up cosmetic composition.

12. The cosmetic composition according to claim 2, wherein the particles of ferric oxide have been subjected to a surface treatment with oxides, hydroxides, and/or hydrous oxides of one or more metal elements selected from the group consisting of silicon, aluminum, zinc, and iron.

13. The cosmetic composition according to claim 1, wherein the composite oxide of titanium and iron coating the part of the surface of the scale-like base member not covered by the particles has the formula

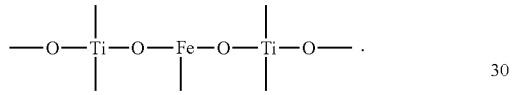

\* \* \* \* \*